(12) United States Patent
Nagle et al.

(10) Patent No.: US 6,960,703 B2
(45) Date of Patent: Nov. 1, 2005

(54) GRAIN PRODUCTION METHOD FOR MAIZE STARCH WITH NOVEL FUNCTIONALITY

(75) Inventors: Barry Nagle, Carmel, IN (US); Gary Apel, St. Anne, IL (US); Joseph L. Emling, Fishers, IN (US)

(73) Assignee: National Starch and Chemical Investment Holdings Corporation, New Castle, DE (US)

( * ) Notice: Subject to any disclaimer, the term of this patent is extended or adjusted under 35 U.S.C. 154(b) by 235 days.

(21) Appl. No.: 10/090,969

(22) Filed: Mar. 6, 2002

(65) Prior Publication Data

US 2003/0167987 A1 Sep. 11, 2003

(51) Int. Cl.[7] .............................. A01H 1/00; A01H 1/02; A01H 1/06; C12P 19/04
(52) U.S. Cl. ...................... 800/275; 800/263; 800/270; 800/274; 800/320.1
(58) Field of Search ................................. 800/263, 270, 800/274, 275, 320.1

(56) References Cited

U.S. PATENT DOCUMENTS

| | | | | |
|---|---|---|---|---|
| 4,051,629 A | * | 10/1977 | Galinat ........................ 800/263 |
| 4,428,972 A | | 1/1984 | Wurzburg et al. ........... 426/578 |
| 5,004,864 A | * | 4/1991 | Robertson et al. .......... 800/264 |
| 5,535,688 A | | 7/1996 | Kaufman ...................... 111/52 |
| 5,675,064 A | * | 10/1997 | Pearlstein et al. ....... 800/320.1 |
| 5,704,160 A | | 1/1998 | Bergquist et al. ............... 47/58 |
| 5,706,603 A | | 1/1998 | Bergquist et al. ............... 47/58 |
| 5,954,883 A | | 9/1999 | Nagle et al. ................... 127/36 |
| 6,218,155 B1 | | 4/2001 | Chang et al. ................ 435/101 |
| 6,274,792 B1 | | 8/2001 | Chang et al. ................ 800/298 |

FOREIGN PATENT DOCUMENTS

| | | |
|---|---|---|
| EP | 0 572 412 B1 | 5/1997 |
| WO | WO 95/35026 | 12/1995 |

OTHER PUBLICATIONS

Sprague, G.F. et al, "Corn Breeding", Corn and Corn Improvement—Agronomy Monograph No. 18, 1988, pp. 305–362.

Wych, Robert D., "Production of Hybrid Seed Corn", Corn and Corn Improvement—Agronomy Monograph, 1988, pp. 561–607.

Palagyl, A. et al, "Maize Hybrid Seed Production By The Mutual Random Melting Of The Parental Components", Cereal Research Communications, vol. 24, No. 3, 1995, pp. 307–316.

* cited by examiner

*Primary Examiner*—David T. Fox
(74) *Attorney, Agent, or Firm*—Karen G. Kaiser

(57) ABSTRACT

A novel method of producing maize grain with desirable functionality has been developed involving planting two different maize hybrids within the same field. The two maize hybrids are planted in alternating blocks of rows. One hybrid is male sterile such that the second hybrid provides pollen for the entire field. This leads to blocks of two separate types of grain which may be harvested and processed separately.

10 Claims, No Drawings

GRAIN PRODUCTION METHOD FOR MAIZE STARCH WITH NOVEL FUNCTIONALITY

BACKGROUND OF THE INVENTION

The present invention relates to a method of producing two types of hybrid maize in a field such that they may be harvested independently.

Maize is a commodity grain in the United States used for a variety of applications including as a human food source, an animal feed, and as a source of carbohydrate, oil, protein, and fiber. However, there exists at present a growing market for maize with special end-use properties which are not met by maize grain of standard composition. Most commonly, specialty maize is differentiated from "normal" field maize by altered endosperm properties, such as an overall change in the degree of starch branching (waxy maize and amylose extender), increased accumulation of sugars or water-soluble polysaccharides (sugary, shrunken, and supersweet maize) or alterations in the degree of endosperm hardness (food grade maize or popcorn).

The need for such specialty maize arises, inter alia, from the need for starches with specific functionality or properties for use in a variety of industrial applications including paper additives such as sizings, adhesives, food components such as thickeners, industrial and medical absorbants, pharmaceutical excipients, cosmetics, and delivery systems such as emulsifiers.

Virtually all commercial maize produced in the United States, Canada, and Europe, and much of the maize produced in South America, is produced from hybrid seed. The production of maize hybrids requires the development of elite maize inbred lines that demonstrate good general and specific combining ability in order that they produce agronomically superior hybrids. Among the traits that plant breeders select for in producing hybrids are high yield, fast grain drydown, and resistance to specific plant diseases and insects.

Once elite inbreds have been developed, they may be used in several ways to produce commercial hybrid seed. The majority of hybrid seed produced in the United States is of the single cross type. Two inbred lines are intermated to give rise to what is termed an F1 single cross hybrid (A×B). In some instances, the female parent in the cross is itself an F1 hybrid, so that a three-way cross hybrid is produced with the genotype of (A×B)×C. More rarely, a four-way cross hybrid is produced, with both male and female parents as F1 hybrids, resulting in a genotype of (A×B)×(C×D). In all cases, the resulting kernels from this intermating are sold as seed to commercial growers who ultimately harvest F2 grain from the crop for on farm use or commercial sale.

In addition to possessing the proper combination of genetic factors to produce elite hybrids, the inbreds themselves must be reasonably vigorous to support the demands of modern seed production. This can be illustrated by a description of how single cross hybrids are produced commercially. To control the direction of pollination and assure the harvest of predominantly hybrid seed, seed production fields are typically designed so that 4 rows of inbred maize plants serving as females (male sterile) alternate with 1 row of inbred maize plants serving as males (male fertile). The female plants are rendered male sterile such that ovules borne on these female plants are then fertilized by pollen produced by the male plants, and the resulting hybrid seed borne on the female plants is harvested, cleaned, sized, and treated prior to sale to commercial growers. To produce this hybrid seed economically the male inbred plants need to reliably shed sufficient pollen to fertilize the female plants over a variety of climatic conditions. The hybrid seed borne on the female inbred plants need to be of high quality to allow good germination and early plant vigor in the commercial grower's field, and the female plants themselves need to stand and retain ears until the time of harvest.

There are numerous breeding schemes used to produce inbred lines of maize including the pedigree system of breeding, backcross conversion, and recurrent selection. All of these schemes are labor and capital intensive, each requiring many years of effort to allow for both recombination of genetic information and selection to eventually produce elite inbred lines. The rapidity with which satisfactory inbred lines can be developed is determined to a large degree by the nature and number of traits that the lines must possess as dictated by the plant breeder. The addition of novel or unusual traits, especially if controlled by many genes as in the case of oil content, would significantly increase the time and effort required to produce the desired lines.

More recently, alternative methods have been developed for producing maize hybrids with unique functionality. For example, U.S. Pat. Nos. 5,704,160 and 5,706,603 introduce methods of producing maize with enhanced traits such as high oil. The entire field of maize is then harvested together, resulting in a single intermediate trait maize. In the alternative, only one type of maize is harvested and the other is allowed to go to waste.

Development of corn hybrids with unique starch functionality is similar to commercial corn breeding. Altered starch functionality can be achieved by incorporating recessive forms of genes involved in the starch biosynthetic pathway. These genes are commonly referred to as kernel mutant genes. Kernel mutant genes can often cause reduced starch accumulation and difficulties in the wet milling operations designed to isolate the starch from other fractions of the corn kernel.

Surprisingly, it has now been discovered that by planting two different maize hybrids in alternating blocks of rows of sufficient width to efficiently harvest separately, maximum functionality of the maize kernel trait may be achieved. Further, by using one hybrid which is homozygous for two recessive kernel mutant genes and a second hybrid which is homozygous for only one of the two recessive genes, the desired functionality of the starch may be realized without the usual drawbacks of double recessive hybrids.

SUMMARY OF THE INVENTION

This patent pertains to a novel method of producing corn grain with desirable starch functionality by planting two different maize hybrids within the same field. One maize hybrid is homozygous for two recessive genes conditioning the composition of starch and the second maize hybrid is homozygous recessive for one of these same genes and carries the wild type or dominant allele at the second gene loci. The two maize hybrids are planted in alternating blocks of rows. One hybrid is rendered male sterile such that the second hybrid provides pollen for the entire field. This leads to blocks of two separate types of grain which may be harvested and processed separately.

Heterozygous, as used herein, is intended to mean a genetic condition existing when different alleles reside at corresponding loci on homologous chromosomes.

Homozygous, as used herein, is intended to mean a genetic condition existing when identical alleles reside at corresponding loci on homologous chromosomes.

Hybrid, as used herein, is intended to mean any offspring of a cross between two genetically unlike inbred lines.

Inbred, as used herein, is intended to mean a substantially homozygous variety.

Male sterile, as used herein, is intended to mean that the plant does not produce functional pollen as a consequence of any mechanism including without limitation mechanical or hand detasseling, chemical sterility, or genetic sterility such as cytoplasmic male sterility which renders the tassel non-functional.

Unless otherwise stated, dominant genes are represented by capital letters and recessive genes by lower case letters. The endosperm of maize is triploid and contains three alleles of a gene. For generic hybrids, A and B are used to represent the two traits. Thus, aaabbb would represent a hybrid homozygous recessive for generic trait A and generic trait B while aaaBbb would represent a hybrid homozygous recessive for generic trait A and heterozygous for trait B with one dominant or wild type allele and two recessive or mutant alleles.

The remaining genes of the hybrids used may be homozygous recessive or dominant or heterozygous. For example, it is intended to cover the crossing not only of the described aaaBBB with aaabbb, but also the crossing of aaaBBBccc with aaabbbccc.

DETAILED DESCRIPTION OF THE INVENTION

This patent pertains to a novel method of producing maize grain with desirable functionality by planting two different maize hybrids within the same field. One maize hybrid is homozygous for two desired recessive genes. The second maize hybrid is homozygous recessive for one of the same genes as the first hybrid and is wild type or homozygous dominant for the other gene.

Recessive gene is intended to include without limitation waxy (wx1), sugary-1 (su1), sugary-2 (su2), sugary-3 (su3), amylose extender (ae1), dull (du1), horny (h1), shrunken-1 (sh1), shrunken-2 (sh2), floury-1 (fl1), floury-2 (fl2), white endosperm (y1), and the opaque series (o1–o14).

One hybrid is rendered male sterile such that the second hybrid provides pollen for the entire field. It is irrelevant to the present invention which hybrid is chosen to be the male sterile hybrid. The particular choice of male sterile and pollinator determines the resulting genotypes of the starch derived from the two hybrids. As is known in the art, maize endosperm is triploid. The endosperm genotype has two gene doses which are inherited from the female ovule and one gene dose which is inherited from the male pollen. Thus, the choice of which hybrid is sterilized is made according to the desired genetic composition of the F2 grain from the F1 hybrids.

The two maize hybrids are planted in alternating blocks of rows. Each block should be of sufficient width to be effectively harvested using commercially feasible harvesting methods, for example the blocks may be the width of standard harvesting equipment. The blocks are typically at least 4 rows wide. Further, the blocks should not be so wide that the blocks are not effectively pollinated. The blocks are therefore typically no more than 16 rows wide. For example, the hybrids may be planted, without limitation, in 6×6 (6 alternating rows of each hybrid), 8×8, 12×12, 12×6, 12×4 or 16×16 blocks.

This leads to blocks of two separate types of grain which may be harvested and processed separately. By keeping the grain from the two hybrids separate, full advantage of the functionality of each grain may be achieved. Such advantage is not realized when the grains are harvested together as you dilute the functionality of one hybrid with that of the other. For example, if a male sterile mutant of recessive traits A and B (aaabbb) and a male fertile mutant of recessive trait A (aaaBBB) are planted in 8×8 blocks in a field and the seeds are harvested separately, maize which is homozygous A recessive and homozygous B dominant (aaaBBB) and maize which is homozygous A recessive with two doses of recessive B (aaaBbb) starches may be sold separately and the functionality of each grain may be fully realized. If the two hybrids are interplanted in the traditional way such that the seeds are harvested together, the resultant starches are a mixture of the two genotypes aaaBBB or aaaBbb and the unique functionality of each genotype can not be realized.

EXAMPLES

The following examples are presented to further illustrate and explain the present invention and should not be taken as limiting in any regard.

Example 1

Production of Waxy Maize with One or Two Doses of the Sugary-2 Gene

A. A male sterile mutant of waxy/sugary-2 (wxwxwxsu2su2su2) and a male fertile mutant of waxy (wxwxwx) are planted in 8×8 blocks in a field. The seeds are harvested separately, resulting in waxy maize (wxwxwx) and waxy maize with two doses of recessive sugary-2 gene (wxwxwxSu2su2su2).

B. A male fertile mutant of waxy/sugary-2 (wxwxwxsu2su2su2) and a male sterile mutant of waxy (wxwxwx) are planted in 8×8 blocks in a field. The seeds are harvested separately, resulting in waxy maize with one dose of recessive sugary-2 (wxwxwxSu2Su2su2) and waxy maize with three doses of recessive sugary-2 (wxwxwxsu2su2su2).

Example 2

Production of Waxy One and Two Dose White Endosperm

A. A male sterile mutant of waxy/white endoperm (wxwxwxy1y1y1) and a male fertile mutant of waxy (wxwxwx) are planted in 12×6 blocks in a field. The seeds are harvested separately, resulting in waxy maize (wxwxwx) and waxy maize with two doses of recessive white endosperm (wxwxwxY1y1y1).

B. A male fertile mutant of waxy/white endosperm (wxwxwxy1y1y1) and a male sterile mutant of waxy (wxwxwx) are planted in 12×6 blocks in a field. The seeds are harvested separately, resulting in waxy maize with three doses of recessive white endosperm (wxwxwxy1y1y1) and waxy maize with one dose of recessive amylose extender (wxwxwxY1Y1y1).

Example 3

Production of a Variety of Grains

A variety of grains were produced by the crosses shown below.

| Male fertile mutant | Male sterile mutant | Resultant hybrids |
| --- | --- | --- |
| wx1wx1wx1Su2Su2Su2 | wx1wx1wx1su2su2su2 | wx1wx1wx1Su2Su2Su2 |
| | | wx1wx1wx1Su2su2su2 |
| wx1wx1wx1su2su2su2 | wx1wx1wx1Su2Su2Su2 | wx1wx1wx1Su2Su2su2 |
| | | wx1wx1wx1su2su2su2 |
| wx1wx1wx1Du1Du1Du1 | wx1wx1wx1du1du1du1 | wx1wx1wx1Du1Du1Du1 |
| | | wx1wx1wx1Du1du1du1 |
| ae1ae1ae1Du1Du1Du1 | ae1ae1ae1du1du1du1 | ae1ae1ae1Du1Du1Du1 |
| | | ae1ae1ae1Du1du1du1 |
| ae1ae1ae1du1du1du1 | ae1ae1ae1Du1Du1Du1 | ae1ae1ae1du1du1du1 |
| | | ae1ae1ae1Du1Du1du1 |
| ae1ae1ae1Su2Su2Su2 | ae1ae1ae1su2su2su2 | ae1ae1ae1Su2Su2Su2 |
| | | ae1ae1ae1Su2su2su2 |
| ae1ae1ae1su2su2su2 | ae1ae1ae1Su2Su2Su2 | ae1ae1ae1su2su2su2 |
| | | ae1ae1ae1Su2Su2su2 |
| y1y1y1wx1wx1wx1Su2Su2Su2 | y1y1y1wx1wx1wx1su2su2su2 | y1y1y1wx1wx1wx1Su2Su2Su2 |
| | | y1y1y1wx1wx1wx1Su2su2su2 |
| y1y1y1wx1wx1wx1su2su2su2 | y1y1y1wx1wx1wx1Su2Su2Su2 | y1y1y1wx1wx1wx1Su2Su2su2 |
| | | y1y1y1wx1wx1wx1su2su2su2 |

What is claimed is:

1. A method of planting comprising the steps of:
   (a) planting two maize hybrids in alternating blocks of rows at least 4 rows wide, wherein:
      (1) the first hybrid is a male fertile maize seed which is homozygous recessive for two desired triploid kernel traits; and
      (2) the second hybrid is a male sterile maize seed which is homozygous recessive for one of the two desired triploid traits and homozygous dominant for the other desired trait;
   (b) permitting the male fertile maize plants to pollinate said male sterile maize plants; and
   (c) harvesting the resulting maize seed from the two hybrids separately.

2. The method of claim 1, wherein the maize plants have been rendered male sterile by cytoplasmic, genetic, mechanical, chemical, manual or a combination of such methods.

3. The method of claim 1, wherein the hybrids are planted in blocks of rows×rows selected from the group consisting of 6×6, 8×8, 12×12, 12×6, 12×4, and 16×16.

4. The method of claim 1, wherein the two desired recessive traits are selected from the group consisting of waxy (wx1), sugary-1 (su1), sugary-2 (su2), sugary-3 (su3), amylose extender (ae1), dull (du1), horny (h), shrunken-1 (sh1), shrunken-2 (s2), floury-1 (fl1), floury-2 (fl2), white endosperm (y1), and the opaque series (o1–o14).

5. The method of claim 4, wherein the two desired traits are waxy and sugary-2.

6. A method of planting comprising the steps of:
   (a) planting two maize hybrids in alternating blocks of rows at least 4 rows wide, wherein:
      (1) the first hybrid is a male sterile maize seed which is homozygous recessive for two desired triploid kernel traits; and
      (2) the second hybrid is a male fertile maize seed which is homozygous recessive for one of the two desired triploid traits and homozygous dominant for the other desired trait;
   (b) permitting the male fertile maize plants to pollinate said male sterile maize plants; and
   (c) harvesting the resulting maize seed from the two hybrids separately.

7. The method of claim 6, wherein the maize plants have been rendered male sterile by cytoplasmic, genetic, mechanical, chemical, manual or a combination of such methods.

8. The method of claim 6, wherein the hybrids are planted in blocks of rows×rows selected from the group consisting of 6×6, 8×8, 12×12, 12×6, 12×4, and 16×16.

9. The method of claim 6, wherein the two desired recessive traits are selected from the group consisting of waxy (wx1), sugary-1 (su1), sugary-2 (su2), sugary-3 (su3), amylose extender (ae1), dull (du1), horny (h), shrunken-1 (sh1), shrunken-2 (s2), floury-1 (fl1), floury-2 (fl2), white endosperm (y1), and the opaque series (o1–o14).

10. The method of claim 9, wherein the two desired traits are waxy and sugary-2.

* * * * *